US010575755B2

(12) United States Patent
Breisacher et al.

(10) Patent No.: US 10,575,755 B2
(45) Date of Patent: Mar. 3, 2020

(54) COMPUTER-IMPLEMENTED TECHNIQUE FOR CALCULATING A POSITION OF A SURGICAL DEVICE (71) Applicant: Stryker European Holdings I, LLC, Kalamazoo, MI (US)

(72) Inventors: Jochen Breisacher, Teningen (DE); Amir Sarvestani, Freiburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 130 days.

(21) Appl. No.: 14/186,286

(22) Filed: Feb. 21, 2014

(65) Prior Publication Data

US 2014/0243658 A1 Aug. 28, 2014

(30) Foreign Application Priority Data

Feb. 25, 2013 (EP) .................................... 13000944

(51) Int. Cl.
*A61B 5/06* (2006.01)
*A61B 34/20* (2016.01)
*A61B 90/00* (2016.01)

(52) U.S. Cl.
CPC .............. *A61B 5/061* (2013.01); *A61B 34/20* (2016.02); *A61B 2034/2055* (2016.02);
(Continued)

(58) Field of Classification Search
CPC .......................... A61B 5/061; A61B 19/5212
See application file for complete search history.

(56) References Cited

U.S. PATENT DOCUMENTS 6,216,029 B1 * 4/2001 Paltieli ................ A61B 8/0833
600/411
6,934,575 B2 8/2005 Ferre et al.
(Continued)

FOREIGN PATENT DOCUMENTS

| CN | 101023887 A | 8/2007 |
|---|---|---|
| EP | 266432 A1 | 11/2013 |
| WO | WO9927837 A2 | 6/1999 |

OTHER PUBLICATIONS

European Search Report for Application 13000944.2 dated Jul. 31, 2013, 6 pages.
(Continued)

*Primary Examiner* — Jonathan Cwern
(74) *Attorney, Agent, or Firm* — Howard & Howard Attorneys PLLC (57) ABSTRACT A computer-implemented technique for calculating a position of a surgical device relative to a patient region imaged by an imaging device is described. One of the surgical device and the imaging device has a predetermined first positional relationship to a marking, and a first camera having a field of view that includes the marking has a predetermined second positional relationship to the other device. The positional relationships may be stored as calibration data. A method realization of the technique comprises the steps of receiving, from the imaging device, intra-operatively taken first image data representative of the imaged patient region, receiving, from the first camera, intra-operatively taken second image data representative of the marking, and intra-operatively calculating, based on the first and second image data and the calibration data, the position of at least a part of the surgical device relative to the imaged patient region.

12 Claims, 6 Drawing Sheets (52) U.S. Cl.
CPC ................ *A61B 2034/2057* (2016.02); *A61B 2034/2065* (2016.02); *A61B 2090/364* (2016.02); *A61B 2090/378* (2016.02); *A61B 2090/3983* (2016.02)

(56) References Cited

U.S. PATENT DOCUMENTS

| | | | |
|---|---|---|---|
| 2002/0065461 A1* | 5/2002 | Cosman | A61B 6/5247 600/426 |
| 2007/0092123 A1 | 4/2007 | Popescu | |
| 2008/0208041 A1 | 8/2008 | Gilboa | |
| 2010/0121189 A1 | 5/2010 | Ma et al. | |
| 2010/0177185 A1 | 7/2010 | Woerlein et al. | |
| 2011/0245659 A1 | 10/2011 | Ma et al. | |
| 2012/0201421 A1* | 8/2012 | Hartmann | A61B 6/12 382/103 |
| 2014/0171787 A1* | 6/2014 | Garbey | A61B 5/061 600/424 |
| 2014/0375822 A1* | 12/2014 | Jain | A61B 5/06 348/187 |

OTHER PUBLICATIONS

English language abstract for CN101023887 extracted from espacenet.com database on May 6, 2019, 1 page.

* cited by examiner

COMPUTER-IMPLEMENTED TECHNIQUE FOR CALCULATING A POSITION OF A SURGICAL DEVICE

RELATED APPLICATIONS

This application claims priority to and the benefit of European Patent Application No. 13 000 944.2 filed on Feb. 25, 2013, the entire contents of which are hereby incorporated by reference.

TECHNICAL FIELD

The present disclosure generally relates to computer-assisted surgery. Specifically, a technique for calculating a position of a surgical device relative to an intra-operatively imaged patient is presented. The technique may be implemented as a method, as a computer-program product, as a computing device and as a system for computer-assisted surgery.

BACKGROUND

Image-guided surgery is often conducted based on pre-operatively taken image data, such as Magnetic Resonance Imaging (MRI) or Computerized Tomography (CT) data. These pre-operatively taken image data can be very accurate if no significant changes occur during surgery. However, during surgery many different factors may affect, for example, tissue movement, and hence cause changes that are not reflected in the images acquired prior to the surgical procedure. In soft tissue areas, these movements are particularly common (in neurosurgery such changes are also referred to as the brain shift problem).

In order to avoid such problems, it has been suggested to work with continuously updated image data during the surgical procedure. To this end, intra-operative imaging approaches are used. These approaches include, for example, real-time ultrasound imaging.

Intra-operatively taken image data give the surgeon live feedback upon placing a surgical device (e.g., a biopsy needle) in a target area of a patient as soon as the surgical device is also in the field of view of the imaging device. A major limitation is that it is difficult to obtain an optimal view of, for example, a tip portion of the surgical device and the target area at all times in the real-time patient image. When, for example, two-dimensional images are used, only the proximal part of the surgical device intersecting the image plane gets visualized.

Since the surgical procedure is often done free hand, where the ultrasound probe and the surgical device can be freely moved and oriented simultaneously, visualization becomes even more difficult. Still, an optimal view is of crucial importance to know where the surgical device is located relative to important anatomical structures. Often an in-plane approach is used to visualize the surgical device in the intra-operative image, wherein the surgical device is mechanically guided within the image plane. However, this guidance limits the possible positional configuration of the imaging device and surgical device.

To guide the surgeon optimally, it would be valuable to know how to adjust the surgical device in order to direct the surgical device to the anatomical region of interest, even before the surgical device gets reproduced in the image. To achieve this, a localization and visualization of the tool relative to the intra-operative image would be desirable. Providing this additional information helps the surgeon for example to hit the target by a direct approach, and prevents the damaging of additional tissue. It also gives additional information to achieve an even more accurate placement of the surgical device.

SUMMARY

It is an object of the present disclosure to provide a computer-implemented technique to efficiently calculate a position of a surgical device relative to an intra-operatively imaged patient.

According to one aspect, a computer-implemented method of calculating a position of a surgical device relative to a patient region imaged by an imaging device is provided. One of the surgical device and the imaging device has a predetermined first positional relationship to a marking, and a first camera having a field of view that includes the marking has a predetermined second positional relationship to the other device. Calibration data indicative of the first and second positional relationships are provided. The method comprises receiving, from the imaging device, intra-operatively taken first image data representative of the imaged patient region, receiving, from the first camera, intra-operatively taken second image data representative of the marking, and intra-operatively calculating, based on the first and second image data and the calibration data, the position of at least a part of the surgical device relative to the imaged patient region.

The imaged patient region may be a two-dimensional region (i.e., an image plane) or a three-dimensional region (i.e., an image volume). The imaging device may or may not detect the surgical device during operation. For example, the calculating step may be performed regardless of whether or not the surgical device is within the image plane or the image volume of the imaging device. The position of the surgical device, or the part thereof, relative to the imaged patient region could thus also be calculated when the surgical device is outside the image plane or image volume of the imaging device. In such a case, the calculated relative position may be used to determine a projection of the surgical device, its trajectory or its projected trajectory with respect to the image plane or the image volume. When the surgical device enters the image plane or image volume and is detectable by the imaging device, the first image data could also be representative of the surgical device (e.g., the surgical device itself could be visualized in the imaged patient region).

As stated above, the calibration data are indicative of positional relationships. The positional relationships can be defined in a mathematical manner, for example by transformation parameters or otherwise. In one implementation, the first positional relationship is defined by a first transformation between a coordinate system of the marking and a coordinate system of the surgical device or of the imaging device, and the second positional relationship is defined by a second transformation between a coordinate system of the first camera and a coordinate system of the other device. The first transformation and the second transformation may each be defined by a set of transformation parameters.

The calibration data may further describe a third transformation between a coordinate system of the imaging device and a coordinate system of the image taken by the imaging device (e.g., of the first image data). Alternatively, or additionally, the calibration data may describe a fourth transformation between a coordinate system of the first camera and a coordinate system of an image taken by the first camera (e.g., of the second image data). Each of the third transformation and the fourth transformation may be defined by a set of transformation parameters. In one implementation, at least one of the third transformation and the fourth transformation is defined by a projection function (e.g., from three spatial dimensions into two dimensions of an image plane).

The marking may at least partly be visible to the first camera. Moreover, the marking may generally be such that its (e.g., geometric) properties can be determined from the second image data. The calibration data may further describe geometric properties of the marking. The geometric properties of the marking may be defined in various ways. In one implementation, the marking comprises a plurality of individual markers (e.g., 3, 4 or more). In such an implementation the geometric properties of the marking may be defined by the positions of the markers relative to each other in a coordinate system of the marking. According to another implementation, the marking is a two-dimensional pattern or a three-dimensional body, wherein the shape of the pattern or of the body may define the geometric properties of the marking in the coordinate system of the marking.

The calculating step may comprise determining a fifth transformation between the coordinate system of the marking and a coordinate system of at least one of the first camera and an image taken by the first camera. The fifth transformation may be described by a set of transformation parameters. Moreover, the fifth transformation may relate the (known) geometric properties of the marking and a shape of the marking as identified in the second image data taken by the first camera. As an example, the fifth transformation may be defined based on a perspective back-projection from a two-dimensional image plane associated with the first camera to a coordinate system of the marking. In this regard, an equation system of the perspective back-projection of the image taken by the first camera to the coordinate system of the marking may be solved.

The calculating step may comprise determining a position of the surgical device, or the part thereof, relative to the imaged patient area (e.g., in a coordinate system of at least one of the imaging device and an image taken by the imaging device). In this regard, the position of the surgical device, or the part thereof, may be determined based on a sixth transformation. The sixth transformation may be defined by transformation parameters derived from the transformation parameters of one or more of the first to fifth transformations. For example, the position of the surgical device, or the part thereof, in the coordinate system of at least one of the imaging device and the image taken by the imaging device may be determined based on the first transformation, the second transformation and the fifth transformation. The fifth transformation may again be derived from one or more further transformations, for example from the fourth transformation and a seventh transformation, wherein the seventh transformation associates the coordinate system of the marking and the coordinate system of an image taken by the first camera.

The first image data and the second image data may generally be provided for a two-dimensional image plane or for a three-dimensional image volume. In case the first image data are provided for an image plane, the calculating step may comprise determining an image plane intersection of one or more of the surgical device, its projection, its trajectory and its projected trajectory. In a more general approach, the calculating step may comprise determining at least one of a projection, a trajectory and a projected trajectory of the surgical device, or the part thereof, relative to the patient or the imaged patient region.

The method presented herein may further comprise providing, based on the calculated relative position between at least the part of the surgical device and the imaged patient region, computer-assistant guidance to a surgeon for navigating the surgical device, or the part thereof, relative to the patient or imaged patient region. The computer-assistant guidance may in one implementation comprise visualizing the calculated projection, trajectory or projected trajectory of the surgical device, or the part thereof, relative to the imaged patient region (e.g., by superimposing, the projection, the trajectory and/or the projected trajectory of the surgical device on top of the visualized first image data). Alternatively, or in addition, the computer-assistant guidance may comprise one or both of acoustic and haptic feedback.

In one variant, the method presented herein may comprise receiving third image data from a second camera mounted on or in the surgical device. The second camera may, as an option, have a field of view that includes at least a portion of a targeted area of the patient when performing the surgical procedure with the surgical device. The third image data may be visualized. As an example, the third image data may be visualized in a manner superimposed on the first image data. In addition, or as an alternative, the third image data may be visualized together with the visualized computer-assistant guidance (e.g., in an overlaid manner).

The position of the surgical device, or the part thereof, may be calculated in one or multiple degrees of freedom. As an example, the position may be calculated in 4 degrees of freedom, 5 degrees of freedom or 6 degrees of freedom. When the position is calculated in 4 or 5 degrees of freedom, a roll angle of the surgical device and/or depth information for the surgical device (e.g., with respect to a predefined surface such as a body surface of the patient) may not be considered.

Also provided is a computer program product comprising program code portions for performing the steps of any of the methods and method aspects described herein when the computer program product is executed by a computing device. The computer program product may be stored on a computer-readable recording medium, such as a hard disk, CD-ROM, DVD or semiconductor memory. Also, the computer program product may be provided for download via a network connection.

According to another aspect, a computing device for intra-operatively calculating a position of a surgical device relative to a patient region imaged by an imaging device is provided. One of the surgical device and the imaging device has a predetermined first positional relationship to a marking, and a first camera having a field of view that includes the marking has predetermined second positional relationship to the other device. Calibration data indicative of the first and second positional relationships are provided. The device comprises a first data interface configured to receive, from the imaging device, intra-operatively taken first image data representative of the imaged patient region, a second data interface configured to receive, from the first camera, intra-operatively taken second image data of the marking, and a processor configured to intra-operatively calculate, based on the first and second image data and the calibration data, the position of at least a part of the surgical device relative to the imaged patient region.

Each of the first data interface and the second data interface may be realized as a software interface, a hardware interface or a combination thereof. The first data interface and the second data interface may be integrated into a single data interface.

The computing device may further comprise an output interface configured to provide computer-assisted guidance to a surgeon for navigating the surgical device relative to the patient or the imaged patient region. The output interface could be a display device such as a computer monitor or touchscreen. Alternatively, or in addition, the output interface may be configured to provide at least one of acoustic and haptic feedback.

Also provided is a system for computer assisted surgery comprising the computing device, the first camera and the marking presented herein. The system may additionally comprise at least one of the surgical device and imaging device.

According to a first implementation, the first camera is mounted on or in the surgical device, and the marking is provided on the imaging device. According to a second implementation, the first camera is mounted on or in the imaging device, and the marking is provided on the surgical device. The first and second implementations may be combined in such a manner that dedicated first cameras are mounted on or in each of the surgical device and the imaging device. Likewise, dedicated markings may be provided on each of the surgical device and the imaging device.

The surgical device may have a distal end configured for insertion into a body of the patient and a proximal end configured for manipulation by a surgeon. In one realization, the first and/or second predetermined relationship(s) may be predefined with respect to the distal end of the surgical device. When the surgical device is realized as surgical tool, the distal end may be realized by a tool tip. Generally, the surgical device may be one of an injection needle, an ablation probe, a biopsy needle, an electrode, a catheter (e.g., a rigid catheter) or any similar apparatus.

The imaging device may comprise a handheld imaging probe. In such an implementation the first and/or second positional relationship(s) may be predefined with respect to the imaging probe. The imaging device may generally be realized in various forms, for example as an ultrasound imaging device, a microscope, a gamma camera, or an X-ray device.

The system presented herein may further comprise a second camera mounted on or in the surgical device. The second camera may have a field of view that includes at least a portion of the targeted area of the patient. In one implementation, the field of view is directed along a longitudinal axis of the surgical device. Third image data taken by the second camera may be visualized on a display unit or otherwise.

Still further, the system may comprise a projector mounted in or on the surgical device. Optionally, the projector could also be mounted on the imaging device. The projector is configured to project a visualization of data on the patient (e.g., on the patient's body). The visualized data may include the first image data, the calculated position of at least a part of the surgical device (e.g., relative to the patient image), at least one of a projection, a trajectory and a projected trajectory of the surgical device, or the part thereof, and the computer-assisted guidance.

BRIEF DESCRIPTION OF THE DRAWINGS

Further aspects, details and advantages of the present disclosure will become apparent from the following description of exemplary embodiments in conjunction with the accompanying drawings, wherein.

DETAILED DESCRIPTION

In the following description of exemplary embodiments, for purposes of explanation and not limitation, specific details are set forth, such as particular methods, functions and procedures, in order to provide a thorough understanding of the technique presented herein. It will be apparent to one skilled in the art that this technique may be practiced in other embodiments that depart from these specific details. For example, while the following embodiments will partially be described on the basis of an ultrasound imaging device and a surgical needle, it will be evident that the technique presented therein could also be implemented using different types of imaging devices and other surgical devices.

Moreover, those skilled in the art will appreciate that the methods, functions and steps explained herein may be implemented using software functioning in conjunction with a programmed microprocessor, an Application Specific Integrated Circuit (ASIC), a Digital Signal Processor (DSP) or a general purpose computer. It will also be appreciated that while the following embodiments will primarily be described in the context of methods and devices, the present disclosure may also be embodied in a computer program product which can be loaded to run on a computing device or a distributed computer system comprising one or more processors and one or more memories functioning as storage, wherein the one or more memories are configured to store one or more programs that may perform the methods, functions and steps disclosed herein.

Figure 1:
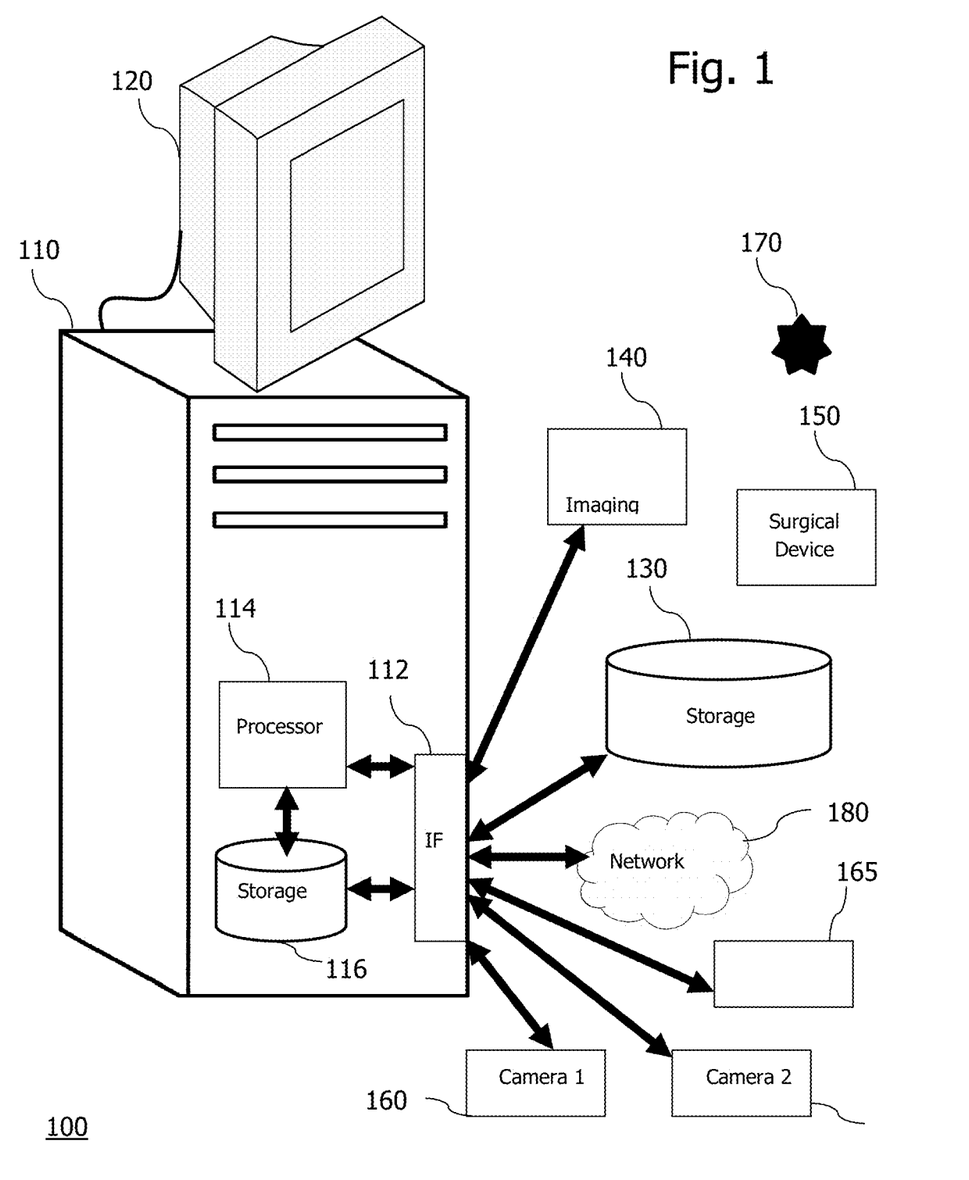
FIG. 1 Schematically illustrates an embodiment of a system for calculating and further processing a position of a surgical device relative to a patient image taken by an imaging device.

FIG. 1 illustrates an embodiment of a system 100 for computer-assisted surgery. As illustrated in FIG. 1, the system 100 comprises a computing device 110 (such a personal, tablet or laptop computer), a display device 120 (such as a touchscreen or computer monitor), and an external storage 130 (such as hard disk or semiconductor memory in which a database or other data system is provided). The system 100 also includes an imaging device 140 configured to intra-operatively take image data of a region of a patient. The imaging device 140 could be a real-time imaging device capable of continuously taking real-time image data of the patient (e.g., one or more image frames per second). Alternatively, the imaging device 140 can be configured to discontinuously take image data immediately before or during the surgical procedure (e.g., only once immediately before or only a few times during the surgical procedure).

Generally, the imaging device 140 could be a free-hand operable device, a mechanically guided device or a fully stationary device. In case the imaging device is a free-hand operable device, it may be configured to continuously take image data of the patient as discussed above. If the imaging device 140 is a mechanically guided or stationery device, it may be configured to discontinuously take patient image data.

The system 100 further includes a surgical device 150 for use in a surgical procedure. As understood herein, also diagnostic or therapeutic treatments of a patient are understood to be surgical procedures. The surgical device 150 can be a free-hand operable device (i.e., without any mechanical guidance), or a guided device. In the latter case, the surgical device 150 may be operated fully automatically or semi-automatically by a robot. Alternatively, a mechanical guidance may be present that constrains a movement of the surgical device 150 by the surgeon.

The display device 120 is configured to visualize image data continuously or discontinuously, taken by the imaging device 140 in the context of the surgical procedure. The display device 120 is further configured to visualize computer-assisted guidance for a surgeon navigating the surgical device 150 as will be described in more detail below. It should be noted that such guidance could also be provided via acoustic or haptic feedback.

As shown in FIG. 1, the system 100 comprises a camera 160 and a marking 170. The camera 160 is configured to intra-operatively take image data of the marking 170. Optionally, a second camera 160A may be provided. The second camera 160A is mounted on or in the surgical device 150 and has a field of view that includes a patient area targeted by the surgical device 150. As an example, when the surgical device 150 has a longitudinal axis directed towards the patient in use, the field of view may generally extend along a longitudinal axis of the surgical device 150. Still further, a projector 165 is provided. The projector 165 is capable of projecting image data provided by one or more of the imaging device 140 and the first camera 160 onto the patient.

The marking 170 may be an active marking (e.g., emitting radiation to be detected by the camera 160). Alternatively, the marking 170 may be a passive marking. In the latter case the marking 170 may have reflecting properties. An additional radiation emitter may then be provided and the camera 160 may be configured to detect the radiation reflected by the marking 170. In another configuration, the marking 170 is simply printed on the imaging device 140 or a carrier that can be rigidly attached to the imaging device 140.

The camera 160 has a predetermined positional relationship to one of the imaging device 140 and the surgical device 150, and the marking 170 likewise has a predetermined relationship to the other device 150, 140. The corresponding relationships are in the present embodiment defined by rigidly (but, optionally, releasably) attaching the camera 160 and the marking 170 to the imaging device 140 and the surgical device 150, respectively.

The marking 170 may be an optical marking, in which case the camera 160 is an optical device. In other configurations, the marking 170 may be an infrared (IR) marking comprising one or multiple IR emitters. In such a case the camera 160 will be an IR device.

In one implementation, the marking 170 comprises multiple individual markers, such as coloured spots or IR diodes. Those markers may have a two- or three-dimensional arrangement. In another implementation, the marking 170 comprises a two dimensional pattern or a three-dimensional body.

Still referring to FIG. 1, the system 100 may further comprises at least one user-operable input device such as a keyboard, a mouse or a trackball (not shown) for generating or triggering the generation of user interaction signals. The user interaction signals may control the operation of the system 100. In one variant, the display device 120 and the input device are integrated into a touchscreen. The touchscreen may be part of a tablet computer.

As shown in FIG. 1, the computing device 110 comprises at least one data interface 112, at least one processor 114 such as a Central Processing Unit (CPU) and an internal storage 116 such as a hard disk or a semiconductor memory for storing program code. The data interface 112 is configured as an input/output interface for establishing a wired or wireless communication between the computing device 110 on the one hand and, on the other hand, the display device 120, the storage 130, the imaging device 140, the cameras 160, 160A, the projector 165 and a computer network 180 (such as a Local Area Network, LAN, and/or the Internet).

The data interface 112 can be realized in the form of one or more hardware components, one or more software components or a combination of one or more hardware components and one or more software components. As an example, the data interface 112 may be realized to comprise one or more Universal Serial Bus (USB) interfaces.

The internal storage 116 or the external storage 130, or both, may store calibration data. Alternatively, or in addition, such calibration data may be downloaded via the computer network 180. The external storage 130 may, for example, at least partially be realized in one or both of the imaging device 140 and the surgical device 150 to store calibration data associated with the respective device. The corresponding calibration data stored in the imaging device 140 and/or the surgical device 150 may be wirelessly read by the computing device 110.

In the present embodiment the calibration data include data indicative of the positional relationships between the camera 160 and the imaging device 140 or the surgical device 150 on the one hand and between the marking 170 and the other device 150, 140 on the other hand. As an example, the calibration data may geometrically define (e.g., by vectors or otherwise) the relative positions between the respective pair of entities 140, 150, 160, 170.

The calibration data may, as an option, further comprise imaging functions of the imaging device 140 and of the camera 160. Such imaging functions may be defined by a respective transformation (e.g., by transformation parameters) between coordinate systems of the imaging device 140 and an image taken by the imaging device 140, and coordinate systems of the camera 160 and an image taken by the camera 160. The images may in each case take a two-dimensional or three-dimensional form.

In a similar manner the positional relationships between the camera 160 and the imaging device 140 or the surgical device 150 and between the marking 170 and the other device 150, 140 could be defined by a respective transformation (e.g., by transformation parameters) between coordinate systems of the camera 160 and the one device 140, 150 and coordinate systems of the marking 170 and the other device 150, 140.

In one variant, the calibration data further comprise a description of (thus known) geometric properties (e.g., a geometric shape) of the marking 170. The description may be provided in a coordinate system of the marking 170. If, for example, the marking 170 includes multiple markers, the description may include vectors pointing from a centre of this coordinate system to each individual marker. In another case, the description may include coordinates describing a contour of the marking 170 (e.g., when the marking 170 is realized as a pattern or body).

In the following, exemplary modes of operation of the system 100 illustrated in FIG. 1 will be discussed in more detail with reference to the remaining drawings. It should be noted that the operational modes discussed herein could also be implemented in a system having a configuration different from that shown in FIG. 1.

Figure 2:
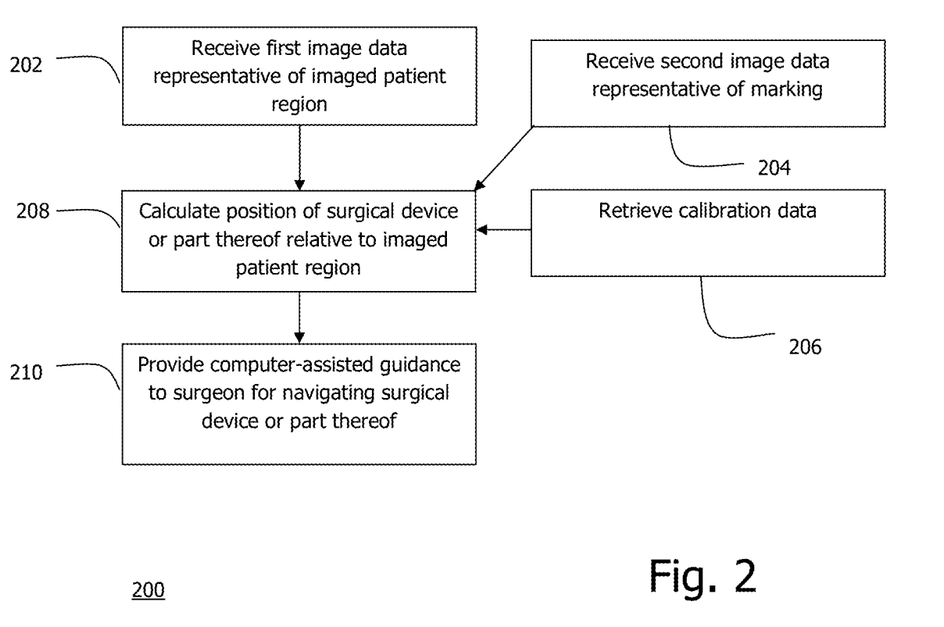
FIG. 2 Is a flow diagram illustrating a method embodiment of the technique presented herein.

The system 100 of FIG. 1 is generally operated to provide computer-assistance during a surgical procedure. The computer-assistance may comprise computer-assisted guidance to a surgeon for navigating the surgical device 150, or a part thereof, relative to the patient. In this regard, FIG. 2 illustrates a flow diagram 200 representative of a method embodiment for providing computer-assisted guidance. It should be noted that the technique presented herein may also be used for purposes other than computer-assisted guidance, such as robotic surgery or the provision of a logging file for later evaluation.

As illustrated in the flow diagram 200, the method embodiment comprise three (or more) dedicated steps of acquiring information. In step 202, first image data representative of an imaged patient region are received. The first image data have been intra-operatively taken by the imaging device 140 and may be, as an option, be continuously updated while the imaging device 140 is in use. In step 204, second image data representative of the marking 170 are received. The second image data have been intra-operatively taken in real-time by the camera 160 and are continuously updated. Step 204 requires that the marking 170 is at least partially in the field of view of the camera 160. An audible or visual warning message may be generated by the system 100 when, during a surgical procedure, the marking 170 (fully or partially) leaves the field of view of the camera 160.

In step 206, calibration data are retrieved (e.g., from the internal storage 116 or the external storage 130). Various types of calibration data that may retrieved have already been discussed above. In the present method embodiment, at least calibration data indicative of the positional relationships between the two pairs of entities 140, 150, 160, 170 are retrieved.

It should be noted that the information acquisition steps 202, 204 and 208 can be performed in any order and also simultaneously. The image data reception steps 202, 204 may in one variant be performed continuously and in parallel over an extended period of time during the surgical procedure. The calibration data retrieval step 206, on the other hand, can be performed only once when setting up the system 100 for a specific surgical procedure.

In step 208, a position of the surgical device 150, or a part thereof, is calculated based on the information acquired in steps 202, 204 and 206. The calculation step 208 is performed intra-operatively and in real-time to determine a position of the surgical device 150 relative to a patient region imaged by the imaging device 140. The position of the surgical device 150 relative to imaged patient region may be exploited to visualize its projection (e.g., on an image plane or image volume) and/or its trajectory (including a trajectory projected on an image plane or an image volume).

Based on the position calculated in step 208, computer assistant guidance to a surgeon is provided in a next step 210. It should be noted that steps 208 and 210 may be performed in parallel and continuously to enable real-time navigation of the surgical device 150. The computer assistant guidance may, for example, comprise displaying the patient image and the position of the surgical device (or its projection, its trajectory, or its projected trajectory, as calculated from the position) on the display device 120.

In the following, the embodiments generally described above in connection with FIGS. 1 and 2 will be explained in more detail with reference to embodiments illustrated in FIGS. 3 to 6. It should be noted that the embodiments of FIGS. 3 to 6 could be implemented using the system 100 of FIG. 1, and therefore the same reference numerals will be used. However, the embodiments of FIGS. 3 to 6 could also be implemented using a system having a different configuration.

Figure 3:
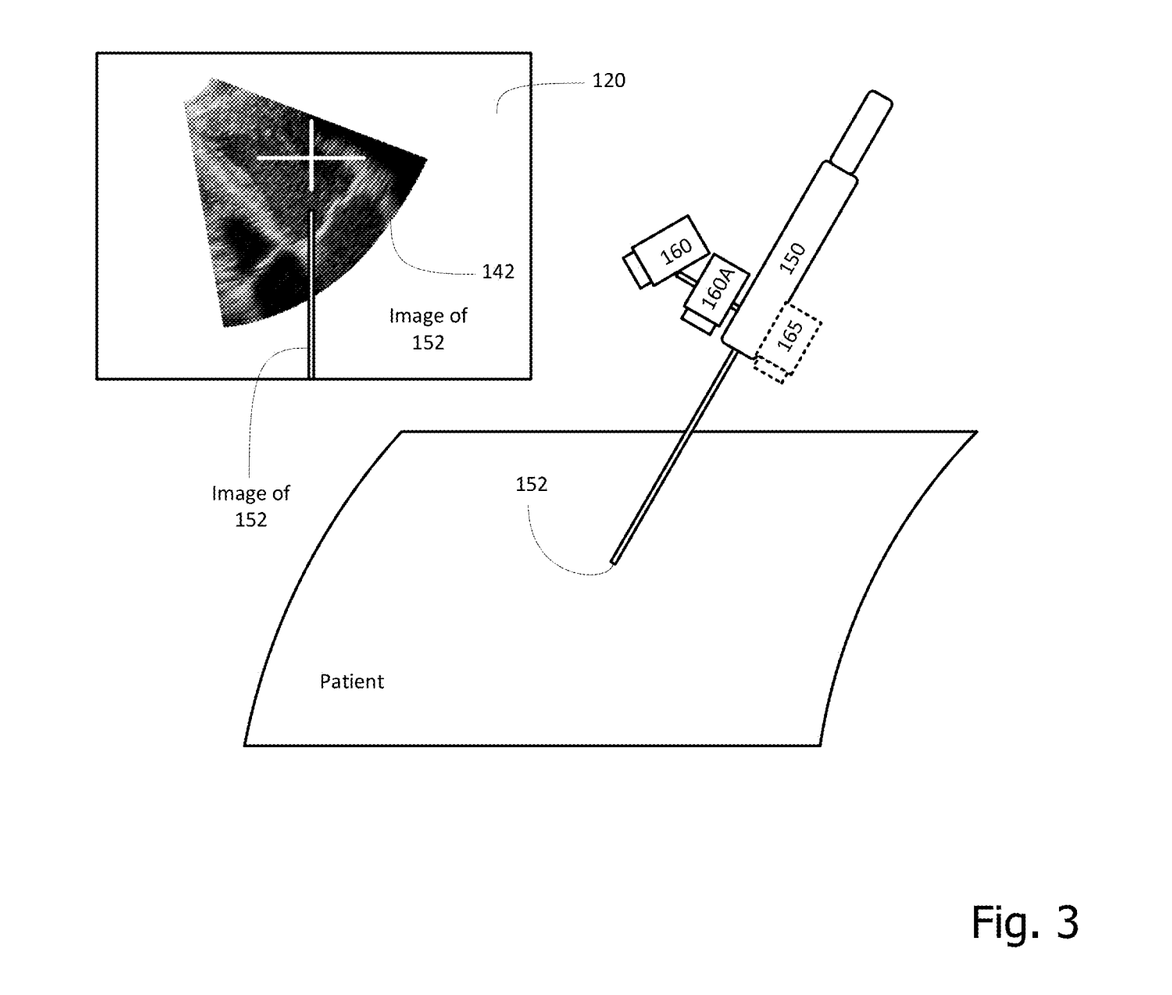
FIG. 3 Schematically illustrates a surgical scenario that makes use of the system embodiment of FIG. 1.

FIG. 3 illustrates a surgical procedure in which a patient is treated using a surgical device in the form of a needle-like instrument 150 (also simply referred to as instrument 150 hereinafter). The instrument 150 could, for example, be realized as biopsy needle or an injection needle. It will be appreciated that the embodiments of FIGS. 3 to 6 could also be realized using a different surgical device, such as an ablation probe, an electrode or a catheter.

As shown in FIG. 3, the instrument 150 has a proximal end 152 configured for insertion into the body of the patient and a distal end 154 in the form of a handle for manipulation by the surgeon. A camera 160 is releasably attached to the instrument 150 remote from its proximal end 152. As explained above, the positional relationship between the camera 160 and the proximal end 152 (e.g., a tool tip) of the instrument 150 is stored as calibration data.

Also shown in FIG. 3 is an imaging device in form of a hand-held ultrasound probe 140 that continuously provides image data in real time. It will be appreciated that in other embodiments other types of imaging devices may be used, such as microscopes, gamma-cameras and X-ray devices.

In the embodiment illustrated in FIG. 3, the ultrasound probe 140 and the instrument 150 are freely positionable by the surgeon, which means that there is no mechanical guidance for any of those two devices. In other embodiments one or both of those two devices may be mechanically guided as needed. Moreover, the ultrasound probe 140 could also be realized in a manner stationery relative to the patient.

The ultrasound probe 140 is equipped with a marking 170. In the present embodiment the marking 170 is realized by 12 individual markers distributed in two dimensions over the ultrasound probe 140. The markers constituting the marking 170 are optical markers, and the camera 160 is an optical camera configured to take image data representative of the relative positions of the markers. In use, the instrument 150 and the ultrasound probe 140 will be arranged such that the camera 160 has a field of view that includes at least a portion of the marking 170 (e.g., 4 or more of the markers).

The marking 170 is rigidly attached to the ultrasound probe 140. In other words, there exists a predetermined positional relationship between the marking 170 and the ultrasound probe 140, that is stored as calibration data.

The ultrasound probe 140 is configured to take image data for a patient region in the form of a two-dimensional image plane 142. That image plane 142 will in use extend into the body of the patient, and the image data will thus be representative of anatomical structures within the patient body. In an alternative embodiment, the ultrasound probe 140, or another imaging device, is configured to take image data for a patient region in the form of a three-dimensional image volume.

According to the technique presented herein, the instrument 150 (e.g., its proximal end 152) will be localized by the system 100 relative to the patient region intra-operatively imaged by the ultrasound probe 140. Once the corresponding positional information has been calculated by the processor 114, the display 120 displays the intra-operatively taken image together with supplemental information to assist the surgeon in guiding (or "navigating") the instrument 150. This additional information may include at least one of the projection of the instrument 150 on the image plane 142 and the projected trajectory of the instrument 150 along its longitudinal axis. The additional information helps the surgeon to align the instrument 150 and move it along an optimal trajectory towards an imaged target area in the patient body very accurately. It should be noted that the corresponding assistance can be provided already before the proximal end 152 enters the image plane 142 of the ultrasound probe 140.

Figure 4:
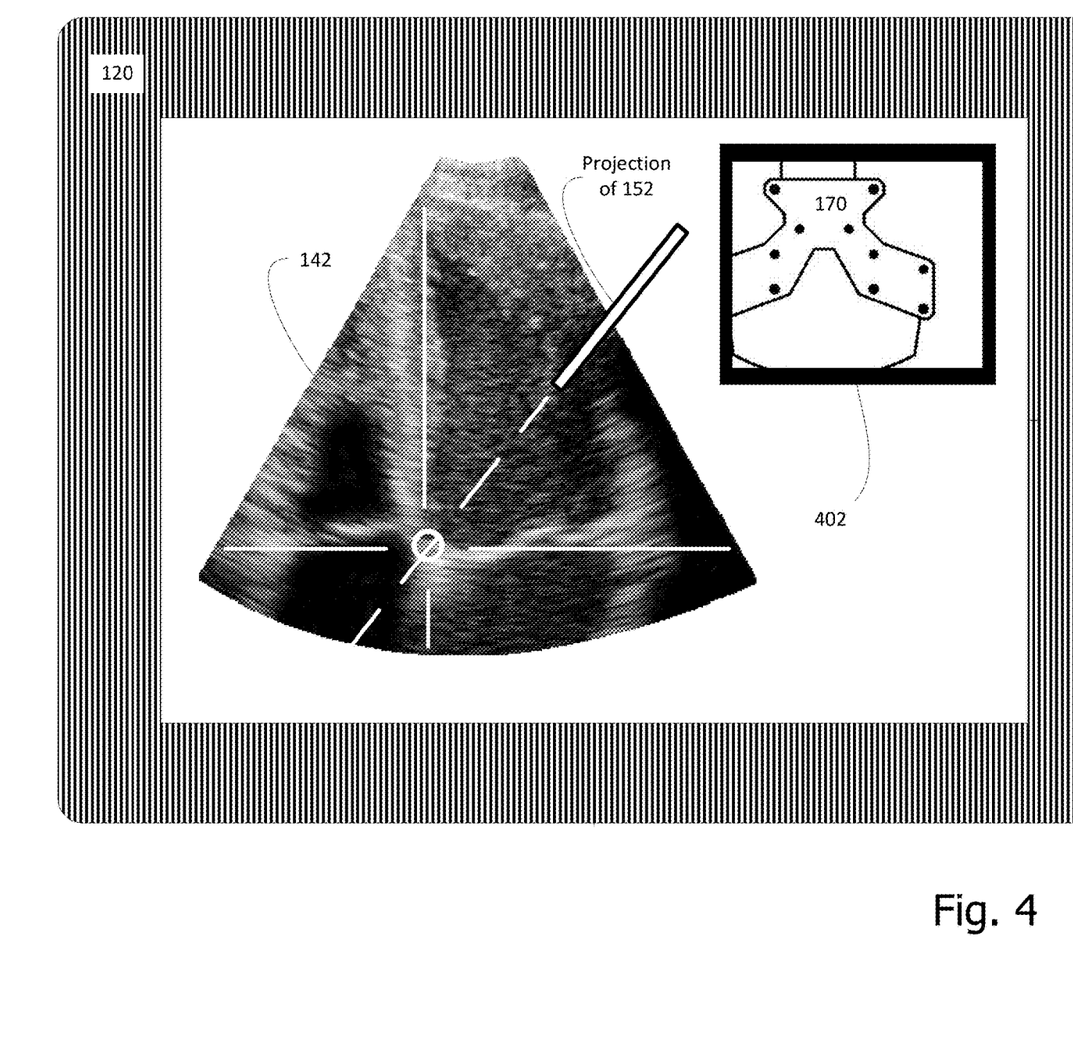
FIG. 4 Schematically illustrates a screen shot as presented to a surgeon during a navigation procedure using the system of FIG. 1.

A typical ultrasound-guided biopsy procedure as illustrated in FIG. 3 will now be described in more detail with additional reference to FIG. 4. FIG. 4 shows the screen of the display unit 120 during the surgical procedure. Specifically, the display unit 120 displays, based on the image data taken by the ultrasound probe 140, the corresponding ultrasound image plane 142. In a smaller window 402, the field of view of the camera 160 (including a portion of the marking 170) is visualized. The window 402 allows the surgeon to control that the instrument 150 and the ultrasound probe 140 are appropriately arranged relative to each other. This means that the field of view of the camera 160 has to include sufficient individual markers of the marking 170 (e.g., 4 or more) so as to allow a calculation of a relative position between the instrument 150 and the image plane 142.

In an initial step of the ultrasound-guided biopsy procedure, the surgeon will place and align the ultrasound probe 140 on the patient's body to visualize the targeted patient area on the display device 120 (see image plane 142 in FIG. 4). After reaching an optimal visualization of the target area, the surgeon keeps the ultrasound probe 140 essentially stable and takes the instrument 150, that here is to hit the target area. As said, in the present embodiment, the instrument 150 is a biopsy needle that permits to take a biopsy at a dedicated target point. When initially orienting the instrument 150 outside the patient's body, the surgeon takes care that the marking 170 on the ultrasound probe 140 is within the field of view of the camera 160 attached to the instrument 150 (see window 402 in FIG. 4).

As soon as the camera 160 can localize the marking 170 on the ultrasound probe 140 in relation to the instrument 150 itself, the system 100 calculates the relative position (and, optionally, its orientation) between the instrument 150 and the imaged patient region and, based on that position, overlays a calculated trajectory of the proximal end 152 of the instrument 150 and an intersection point of the trajectory and the image plane 142 on the displayed ultrasound image. In FIG. 4, the calculated trajectory is visualized by a dashed line, and the intersection point is indicated by a circle. Also, the projection of the current position of the proximal end 152 of the instrument 150 is visualized.

The corresponding surgical information is updated in real-time during the surgical procedure. In this way the surgeon can align the instrument 150 along an optimal approach axis, which allows to hit the target point accurately. The surgeon then moves the instrument 150 along the trajectory while correcting the orientation based on the visual feedback of the display unit 120 until the target point is hit.

Of course, the visual feedback based on the positional and orientational relationship between the ultrasound probe 140 and the instrument 150 can also be a three-dimensional visualization. Moreover, any other feedback (e.g., sound, display of measurements, etc.) which gives the surgeon information how to correct the current position or orientation of the instrument 150 to hit the target point may be provided.

In the following, the calculation steps performed by the processor 114 during the surgical procedure discussed above in connection with FIGS. 3 and 4 will be described in more detail with reference to FIG. 5. It will be appreciated that similar processing steps may be performed in connection with other types of imaging devices and other types of surgical devices.

Figure 5:
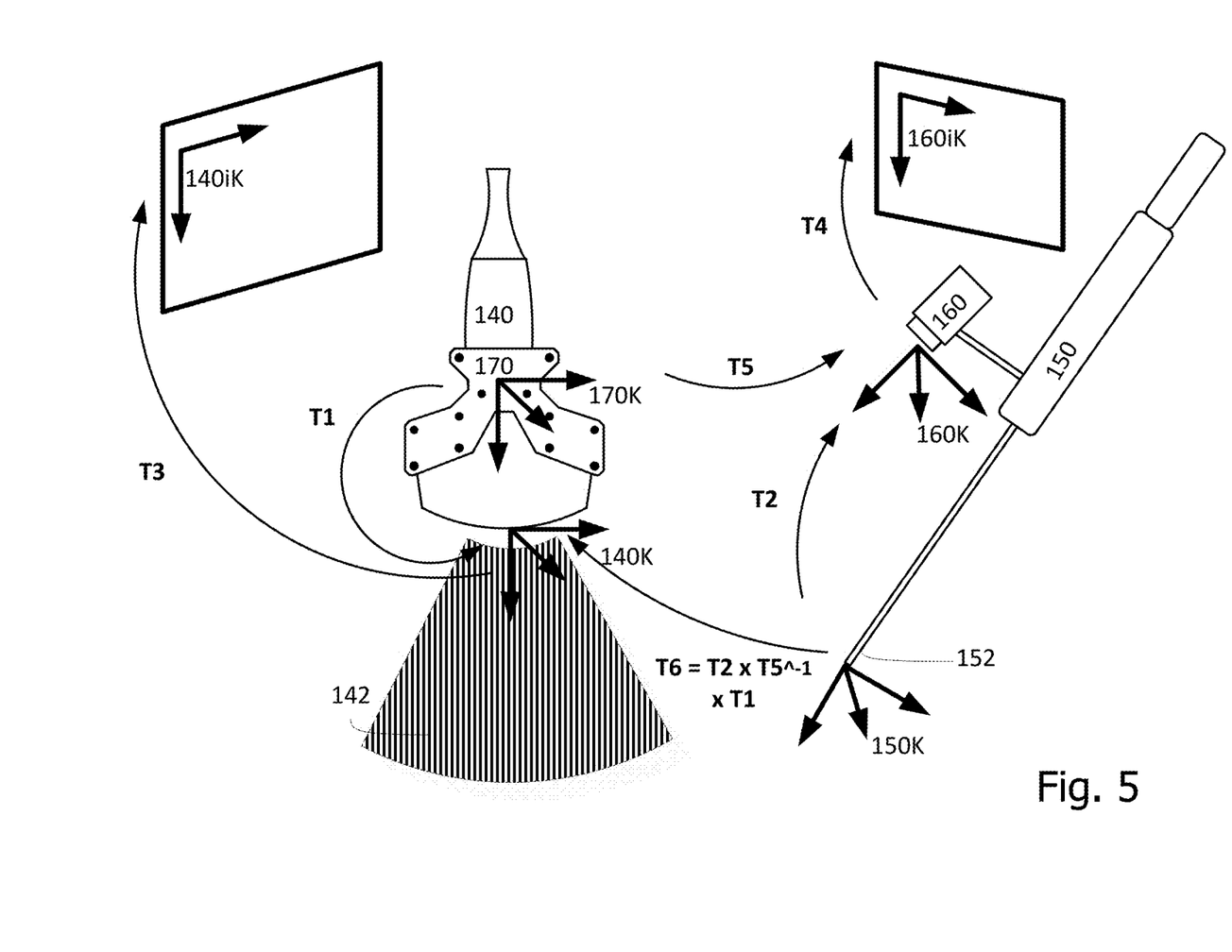
FIG. 5 Is a schematic diagram illustrating transformations in connection with calculating the relative position between the surgical device and image data of the patient.

As shown in FIG. 5, the marking 170 is associated with a marking coordinate system 170K, and the instrument 150 (i.e., its proximal end 152) is associated with an instrument coordinate system 150K. Likewise, the ultrasound probe 140 is associated with an imaging device coordinate system 140K, and the camera 160 is associated with a camera coordinate system 160K. An image taken by the ultrasound probe 140 is associated with an image coordinate system 140iK, and an image taken by the camera 160 is associated with an image coordinate system 160iK.

The positional relationship between the marking coordinate system 170K and the imaging device coordinate system 140K is defined by a first transformation T1 with corresponding transformation parameters. Likewise, the positional relationship between the camera 160 and the instrument 150 is defined by transformation parameters of a second transformation T2 between the camera coordinate system 160K and the instrument coordinate system 150K. The corresponding transformation parameters may be derived by a calibration process already during production (e.g., factory calibration for dedicated instruments or imaging devices) or before the surgical procedure (e.g., on-site calibration for universal adaptation to any instrument 150 or imaging device 140).

The calibration data further describe transformation parameters of a third transformation T3 between the imaging device coordinate system 140K and the associated image coordinate system 140iK. Still further, the calibration data describe transformation parameters for a fourth transformation T4 between the camera coordinate system 160K and the image coordinate system 160iK. The corresponding transformation parameters may be provided by the manufacturers of the camera 160 and the imaging device 140 or by a distributor of the system 100. In certain implementations, the transformation parameters may be provided by the camera 160 and/or the imaging device 140 itself (e.g., dependent on a current zoom factor intra-operatively selected for the camera 160 and/or the imaging device 140).

Also provided as calibration data is the geometric shape of the marking 170 (i.e., the relative positions of the individual markers in the marking coordinate system 170K). Based on that geometric shape of the marking 170 and the (projected) shape of the marking 170 in the image taken by the camera 160 (i.e., in the camera coordinate system 160iK), transformation parameters of a fifth transformation T5 can be determined in real-time by a perspectivistic back-projection from the three-dimensional image plane defined by the image coordinate system 160iK towards the two-dimensional marking coordinate system 170K. While the markers are arranged in a single plane in the present embodiment, their coordinates are still represented in three dimensions here.

The transformation parameters of the fifth transformation T5 are calculated by solving the following equation system for each individual marker j:

$$M_{j,160iK} = T4 \cdot T5 \cdot M_{j,170K},$$

wherein $M_{j,160iK}$ is the imaged marker j in the image data of the camera 160 with coordinates relative to the image coordinate system 160iK, and $M_{j,170iK}$ is provided as calibration data and indicative of the marker j with coordinates relative to the marking coordinate system 170K.

Based on knowledge of the transformation parameters associated with the transformations T1 to T5, the position of the instrument 150 (or its proximal end 152) relative to the imaged patient region can be calculated. Specifically, the position of the instrument 150 can be calculated in a coordinate system of one or both of the ultrasound probe 140 and the image taken by the ultrasound probe 140. To this end, the first transformation T1, the second transformation T2 and the fifth transformations T5 are combined. The position of the proximal end 152 of the instrument 150 relative to the image plane 142 of the ultrasound probe 140 can thus be determined by a sixth transformation T6 between the instrument coordinate system 150K and the imaging device coordinate system 160K as follows:

$$T6=T2 \times T5^{-1} \times T1.$$

Knowledge of the transformation T6 then permits to calculate a projection of the trajectory of the instrument 150 on the image plane 142, and the corresponding intersection point. The trajectory and intersection point may in a next step be visualized as illustrated in FIGS. 3 and 4.

Figure 6:
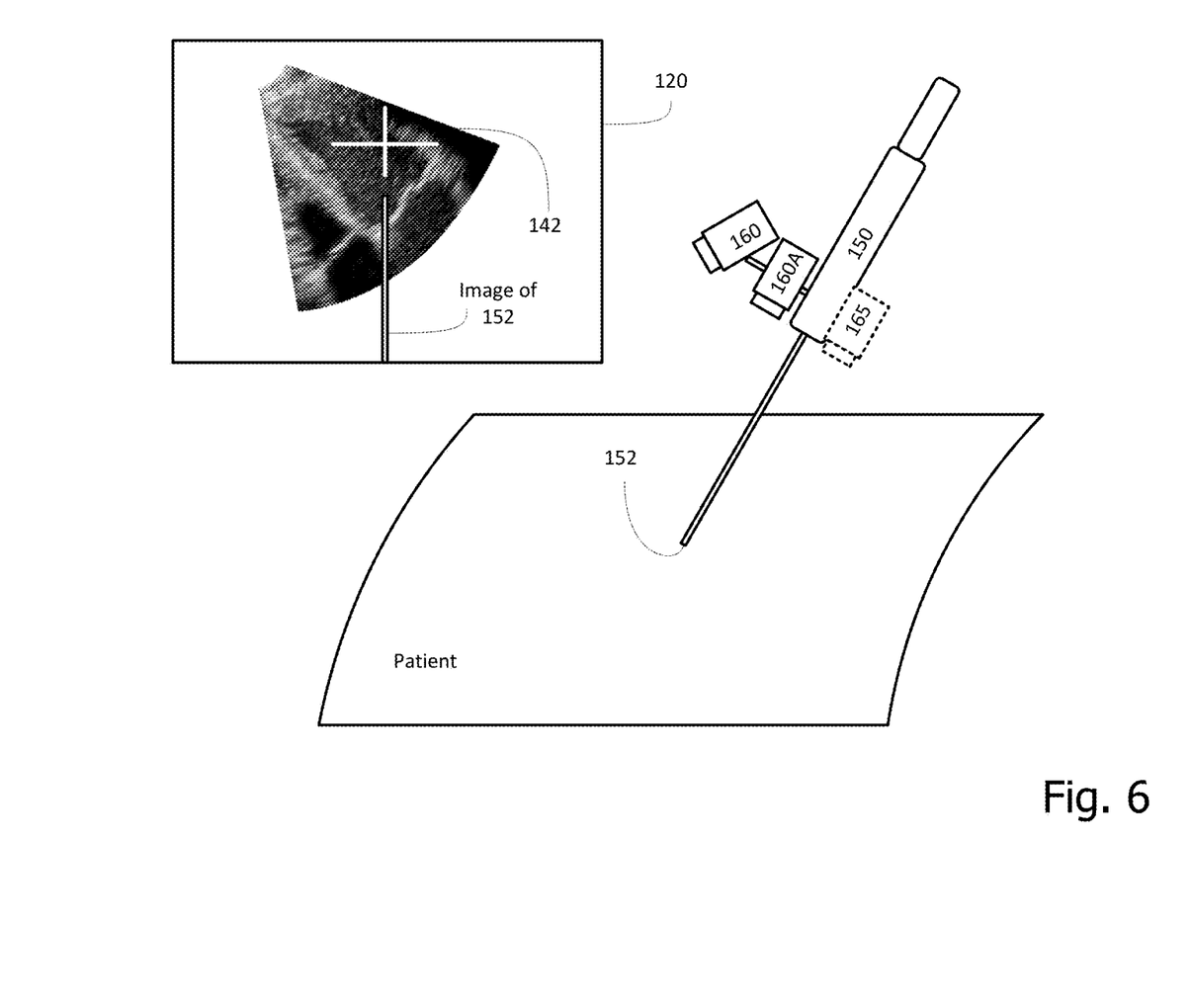
FIG. 6 Schematically illustrates a modified embodiment in connection with providing computer-assisted guidance to a surgeon for navigating the surgical device.

FIG. 6 illustrates a refinement of the embodiment discussed above with reference to FIGS. 3 and 5. Specifically, in the embodiment of FIG. 6 an additional second camera 160A is mounted on the instrument 150. The second camera 160A generally points along the proximal end 152 of the instrument 150 and has a field of view that extends along a longitudinal axis of the instrument 150. This field of view includes a portion of the targeted area of the patient.

The camera 160A is an optical camera, and an image taken by that camera 160A can be superimposed on any other information displayed on the display unit 120. In the specific example of FIG. 6, the image taken by the camera 160A (which includes the proximal part 152 of the instrument 150) is superimposed and aligned relative to the intra-operatively taken image of the ultrasound probe 140, or vice versa. Additional navigation information may be displayed as desired. Specifically, in the example of FIG. 6, the intersection point of the trajectory of the proximal part 152 of the instrument 150 with the image plane 142 is highlighted by a white cross. The visualization indicated in FIG. 6 allows a better hand-eye coordination of the surgeon.

In one variant, a miniaturized projector 165 may be mounted on or in the instrument 150 (e.g., in addition to or instead of the camera 160A). The projector 165 may be used to project a visualization of the image data taken by the ultrasound probe 140 or by any other imaging device on the patient's body. Additionally, or as an alternative, navigation information (e.g., as illustrated in FIGS. 4 and 6) may be projected.

It will be apparent that in the scenarios of FIGS. 3 to 6, the camera 160 and the marking 170 may be swapped. In other words, the camera 160 may be mounted on the ultrasound probe 140 (or any other imaging device), while the marking 170 could be mounted on the instrument 150.

It has become apparent from the description of exemplary embodiments that the technique presented herein permits a precise targeting of a surgical device relative to a target point within a patient's body. The likelihood of missing the target point or the need for newly placing the surgical device can be reduced.

In many of the possible realizations, there will be no need for a line of sight between the marking and a global marking detection system as used in conventional navigation procedures. Since the camera for detecting the marking can be placed directly on the surgical device and/or the imaging device operated by the surgeon, there is a very low likelihood that the surgeon will obstruct the line of sight between the marking and the associated camera.

In an optical realization of the technique, electromagnetic or metal interference can be avoided. Moreover, since revisions of the placement of the surgical instrument can be reduced, also the time required for the surgical procedure can be reduced compared to conventional procedures. As such, cost and complexity can be decreased compared to other navigation solutions that also operate in 4, 5 or 6 degrees of freedom. Further, in many realizations, the need for a global or external localization system can be eliminated.

Possible clinical applications of the technique presented herein include central venous access, cyst aspiration, arthrocentesis, and nerve blocks.

In the foregoing principles, embodiments and various modes of implementing the technique disclosed herein have exemplarily been described. The present invention should not be construed as being limited to the particular principles, embodiments and mode discussed herein. Rather, it will be appreciated that various changes and modifications may be made by a person skilled in the art without departing from the scope of the present invention as defined in the claims that follow.

The invention claimed is:

1. A computer-implemented method of calculating a position of a surgical device relative to a patient region imaged by an imaging device using a marking, wherein the marking is provided on one of the surgical device and the imaging device in a predetermined first positional relationship to the one of the surgical device and the imaging device, and wherein a first camera having a field of view that includes the marking has a predetermined second positional relationship to the other of the surgical device and the imaging device, and wherein calibration data indicative of the first and second positional relationships are provided and further describe relative positions of markers comprised by the marking in a coordinate system of the marking, the computer-implemented method of calculating a position of a surgical device relative to a patient region imaged by an imaging device using a marking comprising:

providing the first camera in or on one of the surgical device and the imaging device;

receiving, from the imaging device, intra-operatively taken first image data representative of anatomical structures within a patient body in an imaged patient region;

receiving, from the first camera, intra-operatively taken second image data representative of the marking;

intra-operatively calculating, based on the first and second image data and the calibration data, the position of at least a part of the surgical device relative to the imaging device based on the imaged patient region, wherein the surgical device is a free-hand operable device, and wherein in the calculation step, a transformation is determined between the coordinate system of the marking and a coordinate system of at least one of the first camera and an image taken by the first camera based on a comparison of the relative positions of the markers as identified in the calibration data and the relative positions of the markers as identified in the second image data taken by the first camera; and providing, based on the calculated relative position of the at least part of the surgical device, computer-assisted guidance to a surgeon for navigating the surgical device, or the part thereof, relative to the patient or the imaged patient region, wherein the calculating step comprises determining at least one of a projection, a trajectory and a projected trajectory of the surgical device, or the part thereof, relative to the imaged patient region, wherein the computer-assisted guidance comprises visualizing the determined projection, trajectory or projected trajectory of the surgical device, or the part thereof, relative to the imaged patient region.

2. The method of claim 1, wherein the first positional relationship is defined by a first transformation between the coordinate system of the marking and a coordinate system of the surgical device or of the imaging device, and wherein the second positional relationship is defined by a second transformation between the coordinate system of the first camera and the coordinate system of the other of the surgical device and the imaging device.

3. The method of claim 1, wherein the calibration data further describe at least one of a third transformation between a coordinate system of the imaging device and a coordinate system of an image taken by the imaging device, and a fourth transformation between the coordinate system of the first camera and the coordinate system of the image taken by the first camera.

4. The method of claim 1, wherein the first positional relationship is defined by a first transformation between the coordinate system of the marking and a coordinate system of the surgical device or of the imaging device, and wherein the second positional relationship is defined by a second transformation between the coordinate system of the first camera and a coordinate system of the other of the surgical device and the imaging device, wherein the position of the surgical device, or the part thereof, relative to the imaged patient region is determined based on the first transformation, the second transformation and the transformation between the coordinate system of the marking and the coordinate system of at least one of the first camera and the image taken by the first camera.

5. The method of claim 1, wherein the calculating step comprises determining the position of the surgical device, or the part thereof, in the coordinate system of at least one of the imaging device and the intra-operatively taken first image data taken by the imaging device.

6. The method of claim 1, further comprising:
receiving third image data from a second camera mounted on or in the surgical device and having a field of view that includes at least a portion of a targeted area of the patient when performing a surgical procedure with the surgical device; and
visualizing the third image data.

7. A computing device for intra-operatively calculating a position of a surgical device relative to a patient region imaged by an imaging device using a marking, wherein the marking is provided on one of the surgical device and the imaging device in a predetermined first positional relationship to the one of the surgical device and the imaging device, and wherein a first camera is configured to have a field of view that includes the marking and has a predetermined second positional relationship to the other of the surgical device and the imaging device, and wherein calibration data indicative of the first and second positional relationships are provided and further describe relative positions of markers comprised by the marking in a coordinate system of the marking, the computing device comprising:

a first data interface configured to receive, from the imaging device, intra-operatively taken first image data representative of anatomical structures within a patient body in the imaged patient region;

a second data interface configured to receive, from the first camera, intra-operatively taken second image data representative of the marking; and a processor configured to intra-operatively calculate, based on the first and second image data and the calibration data, the position of at least a part of the surgical device relative to the imaged patient region, wherein at least one of a projection, a trajectory and a projected trajectory of the surgical device, or the part thereof, is determined relative to the imaged patient region, wherein the surgical device is a free-hand operable device and wherein the processor is further configured to determine a transformation between the coordinate system of the marking and a coordinate system of at least one of the first camera and an image taken by the first camera based on a comparison of the relative positions of the markers as identified in the calibration data and the relative positions of the markers as identified in the second image data taken by the first camera, and wherein the processor is further configured to provide, based on the calculated relative position of the at least part of the surgical device, computer-assisted guidance to a surgeon for navigating the surgical device, or the part thereof, relative to the patient or the imaged patient region, wherein the computer-assisted guidance comprises visualizing the determined projection, trajectory or projected trajectory of the surgical device, or the part thereof, relative to the imaged patient region.

8. The device of claim 7, further comprising an output interface configured to provide computer-assisted guidance to a surgeon for navigating the surgical device relative to a patient or the imaged patient region.

9. A system for computer-assisted surgery, comprising:
a free-hand operable surgical device;
a handheld ultrasound probe configured to image anatomical structures within a patient body in a patient region;
a marking on one of the free-hand operable surgical device and the handheld ultrasound probe in a predetermined first positional relationship to the one of the free-hand operable surgical device and the handheld ultrasound probe with the marking including a plurality of markers-arranged in positions relative to one another;
a first camera coupled to the other one of the free-hand operable surgical device and the handheld ultrasound probe in a predetermined second positional relationship to the other of the free-hand operable surgical device and the handheld ultrasound probe with the first camera including a field of view configured to include the marking;
memory configured to store calibration data indicative of the first positional relationship, the second positional relationship, and the relative positions of the plurality of markers in a coordinate system of the marking;
a controller in communication with the handheld ultrasound probe, and the first camera and the memory with the controller configured to:

receive, from the handheld ultrasound probe, intra-operatively taken first image-data representative of the anatomical structures within the imaged patient region;

receive, from the first camera, intra-operatively taken second image data-representative of the marking;

receive, from the memory, the stored calibration data;

intra-operatively calculate, based on the first and second image data and the stored calibration data, the position of at least a part of the free-hand operable surgical device relative to the imaging device based on the imaged patient region, wherein a transformation is determined between the coordinate system of the marking and a coordinate system of at least one of the first camera and an image taken by the first camera based on a comparison of the relative positions of the markers from the calibration data and the relative positions of the markers as identified in the second image data taken by the first camera, the computing device of claim 7, the first camera and the marking, and wherein at least one of a projection, a trajectory of the surgical device, or the part thereof, is determined relative to the imaged patient region; and provide, based on the calculated relative position of the at least part of the surgical device, computer-assisted guidance to a surgeon for navigating the surgical device, or the part thereof, relative to the patient or the imaged patient region, wherein the computer-assisted guidance comprises visualizing the determined projection, trajectory or projected trajectory of the surgical device, or the part thereof, relative to the imaged patient region.

10. The system of claim 9, wherein the free-hand operable surgical device has a proximal end configured for insertion into the patient body a body of a patient and a distal end configured for manipulation by a surgeon, and wherein the first or second predetermined relationship is predefined with respect to the proximal end of the free-hand operable surgical device.

11. The system of claim 9, further comprising a second camera mounted on or in the free-hand operable surgical device, wherein the second camera has a field of view that includes at least a portion of a targeted area of the patient.

12. The system of claim 9, further comprising a projector mounted in or on the free-hand operable surgical device and configured to project a visualization of the first image data on the patient.

* * * * *